(12) United States Patent
West et al.

(10) Patent No.: US 9,452,239 B2
(45) Date of Patent: Sep. 27, 2016

(54) FABRICATION OF INTERCONNECTED MODEL VASCULATURE

(75) Inventors: Jennifer L. West, Houston, TX (US); Christopher S. Chen, Princeton, NJ (US); Jordan S. Miller, Philadelphia, PA (US); Michael T. Yang, Philadelphia, PA (US)

(73) Assignees: William Marsh Rice University, Houston, TX (US); University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/211,478

(22) Filed: Aug. 17, 2011

(65) Prior Publication Data
US 2012/0058174 A1 Mar. 8, 2012

Related U.S. Application Data

(63) Continuation-in-part of application No. PCT/US2010/024457, filed on Feb. 17, 2010.

(60) Provisional application No. 61/153,096, filed on Feb. 17, 2009.

(51) Int. Cl.
*A61L 27/56* (2006.01)
*A61L 27/38* (2006.01)

(52) U.S. Cl.
CPC ............... *A61L 27/56* (2013.01); *A61L 27/38* (2013.01); *A61L 2400/18* (2013.01)

(58) Field of Classification Search
CPC .... A61L 27/38; A61L 2400/18; A61L 27/56
See application file for complete search history.

(56) References Cited

U.S. PATENT DOCUMENTS

2008/0009955 A1 1/2008 Shimp et al.
2008/0241206 A1 10/2008 Constantz
2011/0270412 A1* 11/2011 Bellan et al. .............. 623/23.72

OTHER PUBLICATIONS

Bellan et al., Soft Matter, 2009, 5, 1354-1357.*
Lewis, Adv. Funct. Mater. 2006, 16, 2193-2204.*
Therriault et al., Nature Materials, vol. 2, Apr. 2003, 265-271 and 347.*
International Search Report and Written Opinion of International Application No. PCT/US 10/24457, dated Feb. 17, 2010.
International Search Report for Application No. PCT/US2010/24457, dated Jun. 23, 2010.
De Vrieze, Sander, et al., "Electrospinning of chitosan nanofibrous structures: feasibility study," Springer Science +Business Media, LLC, May 15, 2007.
International Preliminary Report on Patentability for Application No. PCT/US2010/024457, dated Aug. 23, 2011.

* cited by examiner

*Primary Examiner* — Michael G Hartley
*Assistant Examiner* — Robert Cabral
(74) *Attorney, Agent, or Firm* — Baker Botts L.L.P.

(57) ABSTRACT

Methods of fabricating a substantially interconnected model vasculature, as well as compositions formed from such methods are provided. In some embodiments, the methods may comprise forming a non-woven fiber network comprising a plurality of fibers and a void space; backfilling the void space of the fiber network; and removing the fibers to form a substantially interconnected vascular network.

15 Claims, 11 Drawing Sheets

FABRICATION OF INTERCONNECTED MODEL VASCULATURE

CROSS REFERENCE TO RELATED APPLICATIONS

This application is a continuation-in-part of International Application No. PCT/US2010/024457, filed Feb. 17, 2010 which claims priority to U.S. Provisional Application No. 61/153,096, filed Feb. 17, 2009, the entire disclosures of which are hereby incorporated by reference.

STATEMENT OF GOVERNMENT INTEREST

This invention was made with government support under Grant Number R01 EB005173 awarded by the National Institutes of Health. The government has certain rights in the invention.

BACKGROUND

One of the central goals of tissue engineering and related fields is to create large, whole organ replacements containing a physiologically relevant blood vessel network for the treatment of human disease or injury. While progress has been made in the past several decades, clinical successes have been limited to avascularized constructs for the replacement of thin tissues such as skin (Yannas et al., 1982; Heimbach et al., 1988), cornea (Nishida et al., 2004), and bladder (Atala et al., 2006). The remaining major barrier to creating large, whole organ replacements is one of nutrient and waste transport (Ko et al., 2007; Johnson et al., 2007; Khademhosseini and Langer, 2007). Diffusion alone is sufficient for the growth of human cell aggregates up to several hundred micrometers thick. However, cells at the center of larger cell clusters cannot adequately access nutrients or remove waste by diffusion due to obstruction and metabolism from adjacent cells and accordingly, large cell aggregates develop necrotic cores. What is needed for the successful engineering of living organs or in vitro models of solid tumor growth and malignancy is a combination of convective and diffusive transport—a vascular network.

To enable convective transport within biocompatible materials, three approaches are currently being investigated. The most common approach utilizes various material processing steps such as critical point drying (Dagalakis et al., 1980), gas foaming and salt leaching (Jun and West, 2005), or electrospinning (Pham et al., 2006) to create macroporous structures that can be perfused in vitro for tissue culture. Unfortunately, most of these additional processing steps require reagents or conditions that are cytotoxic and cannot be done in the presence of living cells. Furthermore, because these materials have an open, porous void volume rather than a vessel network, they cannot be matched up with native vasculature in vivo to permit blood flow (Ko et al., 2007). A second approach utilizes co-cultures of endothelial cells and smooth muscle progenitor cells to create random capillary-like structures in 3D inside biomaterials such as collagen gels (Koike et al., 2004). However, the several day time delay required for these cells to generate their own vasculature means that cells at the center of constructs even a few hundred micrometers in diameter may die from lack of adequate nutrient and waste transport before a vessel network is formed. The third approach utilizes photolithographic equipment from the microprocessor industry to create microfluidic structures in a layer-by-layer fashion (Ling et al., 2007; Golden and Tien, 2007). Photolithography requires expensive, proprietary equipment to reach micrometer-scale resolution, and lithography is typically done in cartesian coordinates to yield channels with rectangular cross-sections. In contrast, native vasculature rarely follows straight x-, y-, or z-vectors, and blood vessels have circular cross-sections, meaning that microfluidic scaffolds may not resemble native vasculature sufficiently to recapitulate organ function. Moreover, this mode of fabrication is much too slow to make large models of organ vasculature efficiently. For example, to fabricate only a 1 $cm^3$ model organ structure containing vasculature that makes up 10% of its total volume with micrometer-scale resolution by stereolithography would require patterning 100 billion individual voxels in a serial fashion; even allowing only 1.6 microseconds per voxel (Hahn et al., 2006) this would take 44 hours. At this rate, it would take 3.8 years of continuous fabrication time to create a single construct with the 750 mL of vasculature found in an adult human liver. Extreme optimization or less stringent resolution requirements may allow dramatic time savings, but the exorbitant cost of the equipment and technical expertise needed for this process foreshadows considerable financial hurdles for mass production. While layer-by-layer photomasking is already much faster than raster scanning because a single xy plane of voxels can be fabricated in parallel (Liu Tsang et al., 2007), difficulties in aligning successive layers with high precision and edge-to-edge artifacts that are typically found in these structures highlight the significant technical challenges that are generally associated with photolithography for 3D fabrication at micron-scale resolution. A similar approach of direct-writing in 3D involves a custom-built polyelectrolyte liquid ink extruder which can print three-dimensional webs of micro-periodic structures (Gratson et al., 2004; Therriault et al., 2005). However, the resulting vessels were uniform in diameter, required long timescales for deposition, and had ill-defined inlet and outlet geometry which did not resemble physiologic vasculature.

Basic anatomy demonstrates that identical organs from different people have vascular architectures unique to each of them; yet these organs can still function similarly for each person. Thus, it is not necessarily the exact x, y, and z coordinates of individual vessel components that allow proper functioning for an organ. Rather, the overall transport of blood components that results from vessel architecture is the principal factor what defines healthy and diseased tissue (e.g. vessel tortuosity, red blood cell velocity, $pO_2$, and pH; see FIG. 1).

SUMMARY

In light of the requirements for an effective vascular network, the design criteria for fabricated tissues which mimic normal and tumor vessel network geometry (see FIG. 1) include, but are not limited to, a plurality of branched vessels ranging in size from tens to hundreds of micrometers in diameter and substantially smooth inner walls that may minimize frictional drag and turbulence during fluid flow.

The present disclosure provides, in certain embodiments, a method of forming a substantially interconnected vascular network, comprising: forming a non-woven fiber network comprising a plurality of fibers and a void space; backfilling the void space of the fiber network; and removing the fibers to form a substantially interconnected vascular network. In certain embodiments, the present disclosure provides substantially interconnected vascular networks.

The features and advantages of the present invention will be readily apparent to those skilled in the art upon a reading of the description of the embodiments that follows.

DRAWINGS

Some specific example embodiments of the disclosure may be understood by referring, in part, to the following description and the accompanying drawings.

Figures 8A, 8B, 8C, 8D:
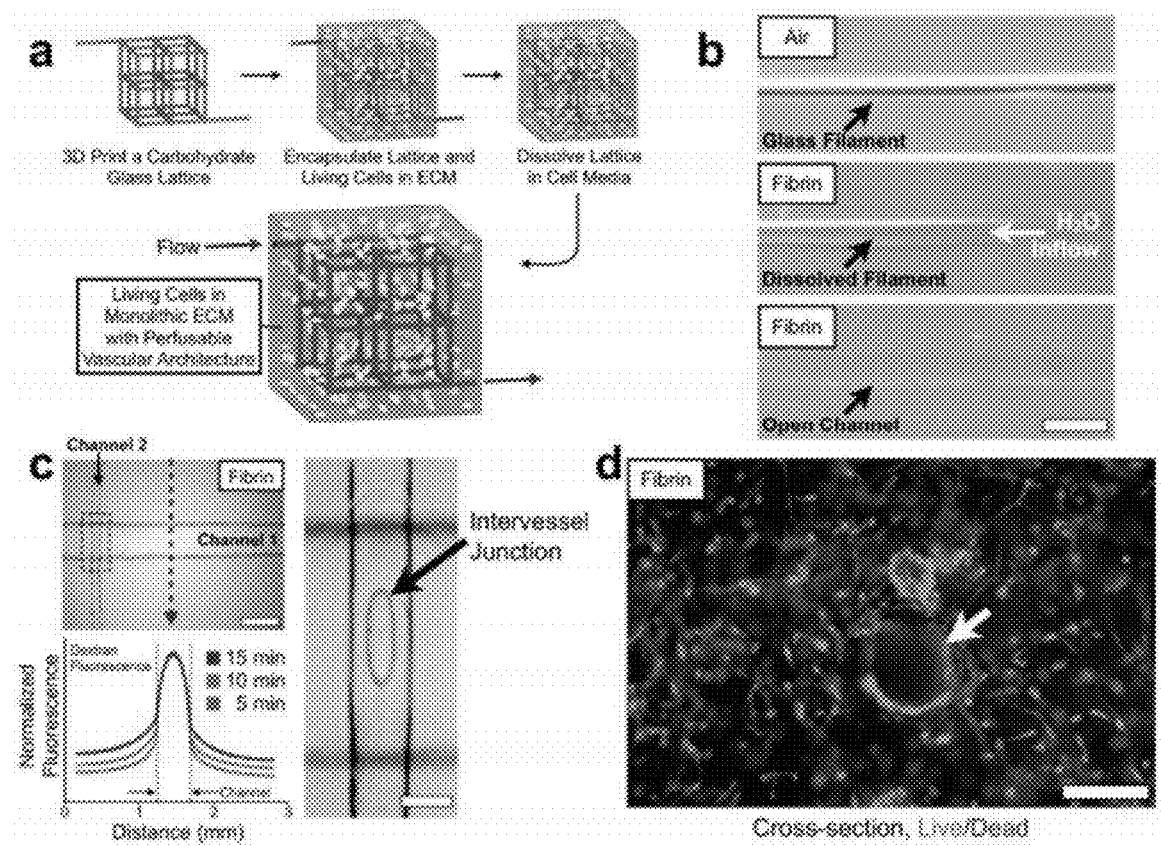

FIG. 8A contains a schematic overview of the process to form monolithic tissue constructs containing patterned vascular architectures and living cells.

FIG. 8B contains images demonstrating the lattice encapsulation in an extracellular matrix (ECM) and subsequent dissolution of the carbohydrate glass lattice and its and removal in saline solution. A single carbohydrate glass fiber (200 μm in diameter, top) is encapsulated in a fibrin gel. Following ECM crosslinking, the gel and filament are immersed in aqueous solution and the dissolved carbohydrates are flowed out of the resulting channel (middle). Removal of the filament yields an open perfusable channel in the fibrin gel (bottom, scale bar=500 μm).

FIG. 8C contains images and graphs showing that a fibrin gel with patterned interconnected channels of different diameters supports convective and diffusive transport of a fluorescent dextran injected into Channel 1 (upper left, phase contrast, scale bar=500 μm). A line plot of normalized fluorescence across the gel and channel (blue arrow) shows a sinusoidal profile in the channel (between dotted black lines) characteristic of a cylinder and temporal diffusion from the channel into the bulk gel. Enlargement of the dotted box region shows an oval intervessel junction between the two perpendicular channels (right, scale bar=100 μm).

FIG. 8D contains a representative cross-section image of HUVEC and 10T1/2 cell co-cultures in fibrin gels after two days in culture. Cells survive and spread near open cylindrical channels (white arrow). Fluorescent Live/Dead staining (green, Calcein AM; red, Ethidium Homodimer). (Scale bar=200 μm.)

Figures 9A, 9B, 9C:
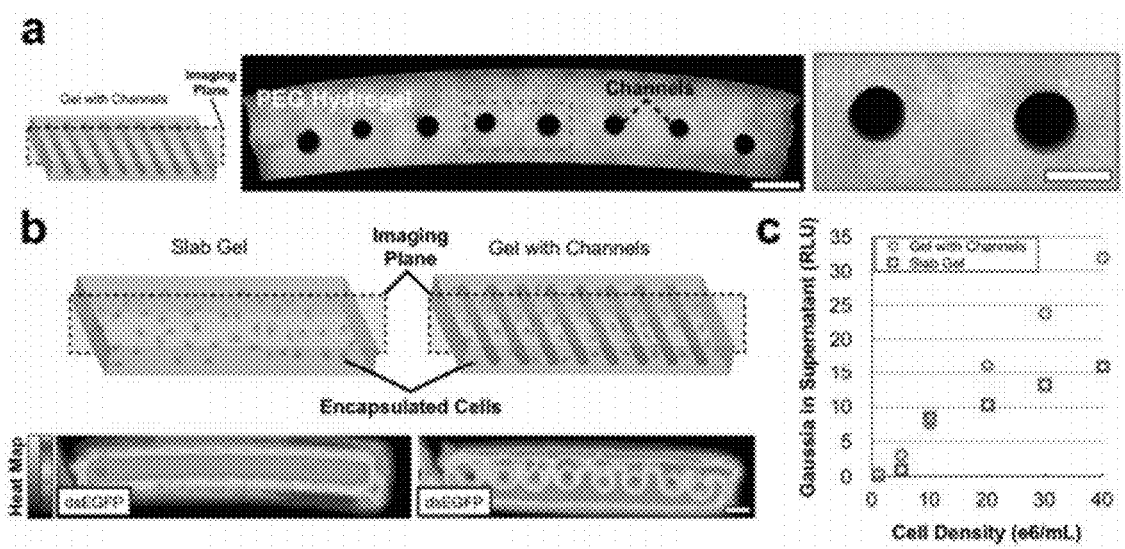

FIG. 9A contains images of a representative cross-section image montage of patterned channels in a PEG hydrogel containing fluorescent beads (Scale bar=2 mm). The area highlighted (green) is enlarged at the right and demonstrates that the gel is monolithic and also has no shadowing artifacts from photopolymerization (Scale bar=1 mm).

FIG. 9B contains images of representative cross-section image montages of PEG hydrogels containing $40 \times 10^6$ HEK cells/mL after three days in culture. The intracellular dsEGFP reporter spatially indicates cells are active at the gel slab perimeter and circumferentially around perfusion channels, but not elsewhere in the gel core. Scale bar=2 mm.

FIG. 9C contains a graph demonstrating a functional enzyme assay of secreted Gaussia luciferase from constructs indicating that the channel architecture preserves cell function even at high cell densities, where function in slab gels quickly falls off.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present invention relates generally to the fabrication of model vasculature. In particular, the present invention relates to methods of fabricating a substantially interconnected model vasculature, as well as compositions formed from such methods.

The present disclosure provides, in certain embodiments, a method of forming a substantially interconnected vascular network comprising: forming a fiber network comprising a plurality of fibers, backfilling the void space of the fiber network (e.g., replica molding, inverse molding), and removing the fibers to form a substantially interconnected vascular network. In addition, the present disclosure also provides substantially interconnected vascular networks formed by the methods described herein. As used herein, the term "fiber network" is defined as an openwork structure in which two or more fibers are interconnected. A fiber network of the present disclosure can serve as a template from which a desired composition of matter is achieved to mimic or recapitulate native human vasculature through various methods as further described below.

In order to, among other things, overcome the shortcomings of the previous methods described above, the methods of the present disclosure may be based, at least in part, on modifications of electrospinning and/or melt extrusion to create model vasculature (see FIG. 2). In some embodiments, a three-dimensional printer may also be utilized. Rather than directly utilizing non-woven fiber mats as macroporous scaffolds (which, as described above are not directly translatable in vivo), the present disclosure is in part based on the finding that the non-woven fiber mats (FIG. 2A) resemble the very vascular structure desired. With proper material choice and parameter optimization during fiber formation, the void space of a vessel network may be filled around the fibers with a material of choice, preferably a biomaterial, (FIG. 2B). The fibers may then be removed to reveal a dense, substantially interconnected vessel network (see FIGS. 2C and 2D).

As mentioned above, in one embodiment, the present disclosure provides a method of forming a substantially interconnected vascular network comprising the step of forming a fiber network comprising a plurality of fibers. In one embodiment, the step of forming a fiber network comprises using electrospinning with an unstable Taylor cone. In another embodiment, the step of forming a fiber network comprises using a plurality of melt extrusion dies. In another embodiment, the step of forming a fiber network comprises using a three-dimensional printer. By way of explanation, and not of limitation, electrospinning and melt extrusion typically utilize a stable Taylor cone or a single die size, respectively, to make fibers with highly uniform diameter distribution. Fibers present in a fiber network of the present disclosure may be solid or hollow. The methods of the present disclosure present a particularly interesting approach to creating vascular networks. For example, in typical electrospinning applications, such as ultrafiltration, it is generally advantageous to have a substantially stable Taylor cone, producing highly uniform fiber diameters with a standard deviation of about ±10% (Pham et al., 2006). However, in using the methods of the present disclosure to form vascular networks, it may be advantageous to utilize an unstable Taylor cone, a range of die sizes, a range of extrusion speeds, a range of extruder translation speeds, or some combination of one or more of these to produce a population of fibers with a much larger diameter distribution (FIG. 2A demonstrates fibers which span an order of magnitude in diameter). Thus, the use of an unstable Taylor cone for electrospinning, a range of die sizes for melt extrusion, a range of extrusion rates, a range of extruder translation speeds, or some combination of one or more of these, may allow a wide range of vessel sizes to be generated during a single fabrication step. Electrospinning may typically be used to create fibers that are much narrower (tens of nanometers up to hundreds of micrometers in diameter) than those that can be created by melt extrusion (tens of micrometers to several centimeters or larger). Since these two techniques together span the full range of vessel sizes found in humans, the combination of melt extrusion and electrospinning can be used in the present disclosure to fabricate a single network with several orders of magnitude of vessel diameters which resemble native vasculature.

In one embodiment, when a fiber network is formed through electrospinning, an electrospinner comprising a spinneret (typically a pipette or a syringe fitted with a needle), a high-voltage power supply, and a collector, which is often a grounded collecting plate (usually a metal screen, plate, or rotating mandrel) may be used. A fiber-forming material is loaded into the spinneret and droplets are allowed to form at the exit from the spinneret, to which an electrostatic field is applied such that fibers are ultimately formed. In another embodiment, when a fiber network is formed through melt extrusion, a fiber-forming material may be placed in an extruder and fibers may be formed using a plurality of melt extrusion dies, a range of extrusion speeds, a range of extruder translation speeds, or a combination thereof. As mentioned above, forming a fiber network according to the methods provided herein produce a population of fibers with a much larger diameter distribution. In yet another embodiment, when a fiber network is formed by a three-dimensional printer, a fiber-forming material may be placed in an extruder and a fiber network may be created by laying down successive layers of the fiber-forming material using the three-dimensional printer.

Fiber-forming materials suitable for use in the present disclosure may comprise any biologically compatible material that is able to form a fiber and subsequently be removed once a material placed around the fibers has solidified. In some embodiments, a fiber forming material may comprise any material that is capable of dissolving or degrading in water. Examples of suitable materials include, but are not limited to, photoresist, agarose, gelatin, carbohydrate(s), including but not limited to, carbohydrates such as sucrose, glucose, fructose, lactose, isomalt (e.g., 1-O-alpha-D-glucopyranosyl-D-mannitol), dextran, cellulose, methylcellulose, and the like, polymers that may degrade over time, such as poly(lactic acid), poly(ethylene glycol) based hydrogels, chitosan, and combinations thereof. In some embodiments, a fiber forming material may comprise any material that is capable of readily dissolving in cell media or physiologically compatible saline solution.

Figure 2A:
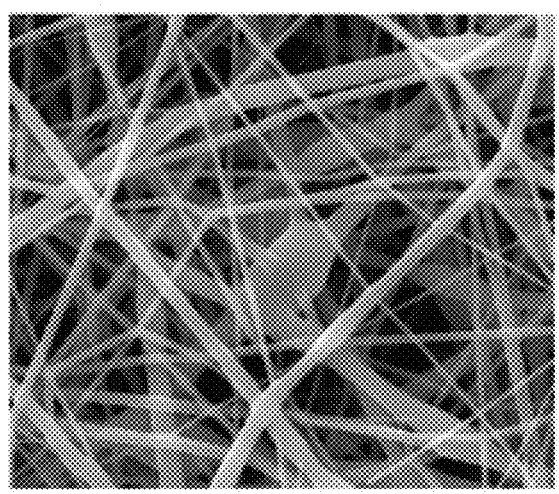
FIG. 2A is an image depicting a network of fibers produced by electrospinning with an unstable Taylor cone (or melt extrusion with a range of die sizes or range of extrusion speeds or extruder translation speeds) with circular cross-sections over a wide range of diameters (at least an order of magnitude) that are reminiscent of normal and tumor vasculature (shown in FIG. 1).

In some embodiments, a fiber network of the present disclosure is allowed to dry before it is backfilled with a biomaterial. In another embodiment, a fiber network can be collected before it has a chance to fully dry. Such a result may create solvent-based fusions at crossing points between different fibers, which may quickly solidify to form a smooth and continuous junction (FIG. 2A). Alternatively, in one embodiment, a fiber network may be heated near its melting temperature or exposed to solvent vapors to anneal adjacent crossing fibers into solid junction points, thus creating a substantially interconnected fiber network. In some embodiments, interconnections between fibers may be controlled by bulk heating, localized heating, and/or surface tension.

In some embodiments, two- or three-dimensional patterns of grounded wires could be used to form a fiber network rather than using a solid grounded collection plate (Gray et al., 2004; Siegel et al., 2007). Once a primary axis is chosen for the fibers and at least one inlet and at least one outlet are defined, these networks may be fused with standard microfluidic channels (created by photolithography, injection molding, or other methods known in the art) made of the same material as the fiber network.

In some embodiments, a fiber network (or portion of a fiber network) of the present disclosure may be surface coated. It may be desirable to surface coat a fiber network of the present disclosure in some embodiments to inhibit wet etching or dissolution of the fiber network. In some embodiments it may be desirable to surface coat a fiber network for stabilization of the fiber network. Examples of suitable surface coatings may include, but are not limited to, poly(lactic acid) (PLA), a solution of polylactic acid in dichloromethane, poly(lactic co-glycolic acid) (PLGA), a solution of PLGA in chloroform, collagen(s), gelatin(s), zein, shellac, starches, petroleum jelly, or other materials, some of which may be known to be directly biocompatible with in vivo blood flow. The surface coating may be designed such that it is removed during fiber network wet etching or dissolution, or alternatively that it remains for a short or long time periods as a basement membrane lining all vessels, much as collagen type IV is known to line all human blood vessels as a native basement membrane. By way of example, not by way of limitation, in some embodiments wherein a fiber network comprises hollow fibers, the fiber network may be surface coated with a thin uniform layer of polylactic acid (PLA, approximately 1 µm thick). The fiber network may then be wet-etched in an aqueous solution, and the remaining PLA network may be pressurized with air or fluid to remain fully inflated. This network is then inverse replica-molded and the PLA network is then wet etched or used to flow fluidic media to nourish cells and then eventually degrades.

In some embodiments, a fiber network and/or coating on a fiber network may be substantially roughened to increase the surface area on these surfaces. By way of example and not by limitation, the roughening process could optionally include direct etching with argon plasma under high vacuum. The roughening process could also optionally include buildup of additional material. By way of example and not by limitation, a fiber network is chilled (approximately 4° C.) and placed above a beaker containing a heated solution of the fiber material or another material (such as an aqueous solution of sugars, 60° C.). The heated solution vaporizes molecules of the solute (in this case, sugar), which then crystallize on the cold fiber network suspended above the heated beaker. The crystallization will grow uniformly off the fiber network dramatically increasing the surface area of the fiber network.

In some embodiments, a fiber network of the present disclosure may comprise zero or more fluidic inlets and zero or more fluidic outlets. In one embodiment, a fiber network may comprise a single inlet and no outlet. This embodiment, especially combined with increasing surface roughness on the fiber network, would allow fiber networks to be constructed which mimic the structure and architecture of human or animal lung which has some of the highest surface area per cubic volume of any human tissue. By way of example and not of limitation, networks which mimic human liver may have one inlet and one outlet, while networks which mimic human lung may have one inlet and zero outlets. Despite these very low numbers of inlets and outlets, the resultant networks may have hundreds, thousands, or more individual filaments or tubes and interconnections which comprise the network. Thus the network design may allow fluidic flow to the entire interconnected network and interstitial space from only a small number of inlet(s) and/or outlet(s).

In order to align the fibers along a principle axis to direct proper inlets and outlets for flow perfusion, many techniques known in the art may be used. Collection onto a spinneret for either electrospinning or melt extrusion, utilizing a spinning extruder, or collecting fibers across two grounded plates separated by some distance (Li et al., 2003; Li et al., 2004) may all be suitable techniques for fiber alignment.

The fiber networks produced by the methods of the present disclosure may comprise up to 95% void volume, making them mechanically weaker than their bulk starting material and potentially difficult to handle and utilize for tissue engineering applications. However, depending on the materials and techniques chosen, the methods of the present disclosure may produce a vascular network comprising fluidic channels that have a channel volumetric density of between 5% and 95%. Such properties may mimic various portions of native vasculature.

As mentioned above, once a fiber network has been formed, the void space of the fiber network is backfilled. Backfilling the void space of the fiber network may be performed with cells, a biomaterial or a combination of biomaterials, or with a wide range of biomaterials that simultaneously contain a suspension of viable cells that can remain viable while forming a vascular network of the present disclosure. As used herein, the term "biomaterial" refers to any material suitable for use in a biological application. Examples of suitable biomaterials may include, but are not limited to, polydimethylsiloxane (PDMS), polyamides, poly(siloxanes), poly(silicones), poly(ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(ethylene glycol) (PEG) hydrogels, poly(methacrylic acid), poly(lactic acid) (PLA), poly(glycolic acid) (PGA), poly(lactide-co-glycolides) (PLGA), polyanhydrides, and polyorthoesters poly(carbonate), poly(acrylo nitrile), poly(ethylene oxide), polyaniline, polyvinyl carbazole, polystyrene and poly(vinyl phenol), polyhydroxyacids, poly(caprolactone), polyanhydrides, polyhydroxyalkanoates, polyurethanes, polysaccharides and poly-biologics such as collagen, albumin, alginate, chitosan, starch, and hyaluronic acid, gelatin, agarose, fibrin, matrigel, glycerol, glycol, and sugar-alcohols, such as mannitol, inositol, xylitol, and adonitol, amino acids such as glycine and arginine, biological polymeric molecules and particularly proteins such as albumin, peptide amphiphiles, and monomers, dimers, and/or oligomers of said materials. As will be recognized by one of ordinary skill in the art, the biomaterial selected will depend on, inter alia, the given application and specifications required. In some embodiments, biomaterials suitable for use in the present disclosure may be crosslinked.

Additionally, the biomaterial or biomaterials of choice can optionally contain pharmaceuticals, proteins, DNA, nanoparticles, or other moieties used for drug delivery applications and/or sensing or combinations of these to enhance or stimulate biological behaviors such as proliferation, differentiation, migration, matrix deposition, or support the formation of more physiologic tissue. In one embodiment, the addition of human bone morphogenic protein (e.g. BMP-2) or DNA plasmids that code for these proteins that stimulate mineralization and bone formation (Bikram et al., 2007) may be used in these vascularized constructs to more appropriately mimic natural vascularized bone.

Any method known to one of ordinary skill in the art may be used for backfilling the void space of the fiber network with a material of interest. Suitable methods include, but are not limited to, centrifugation, sonication, vibration, evacuation, or a combination of some or all of these methods. In some embodiments, once the fiber network has been backfilled with a biomaterial, it is then allowed to harden, cure and/or solidify.

Once the void space of the fiber network has been backfilled, the fibers may be removed to form a substantially interconnected vascular network. In certain embodiments, the step of removing the fibers is performed by wet etching or dissolution. In some embodiments, removing the fibers comprises degrading the fibers. In one embodiment, a fiber network that has been backfilled with a biomaterial may be immersed in a solvent, such as acetone, to remove the fibers. In another embodiment, a fiber network that has been backfilled with a biomaterial may be immersed in a normal cell media or a dilute biocompatible saline solution. As will be recognized by one of ordinary skill in the art, the method selected to remove the fibers may depend upon, inter alia, the given application and specifications required.

In certain embodiments, a combination of surface coating and wet etching or dissolution processes can be repeated before backfilling a biomaterial into a fiber network to convert the fiber network into suitable materials or optionally create multi-layer structures, or optionally create hollow fiber networks.

As mentioned above, in certain embodiments, fiber-forming materials suitable for use in the present disclosure may dissolve readily in cell media or physiologically compatible saline solution. Such a fiber-forming material therefore readily allows fabrication of a fiber network in a wide range of biomaterials which are insoluble in cell media or physiologically compatible saline solution and can optionally be fabricated containing living cells. If the removal of the fiber network is based simply on dissolution, the fabrication of the fiber network is therefore achieved independently of the method by which the biomaterial is crosslinked. By way of example and not of limitation, collagen gels (which crosslink by protein precipitation), fibrin gels (which crosslink by enzymatic activity), agarose gels (which crosslink by polymer chain entanglements), alginate gels (which crosslink by ionic interactions), and photopolymerized gels such as those made from poly(ethylene glycol) diacrylate (which crosslink by covalent polymerization) are all biocompatible materials which are amenable to use with fiber-forming materials which can readily dissolve in cell media or physiologically compatible saline solution.

In light of the requirements for an effective vascular network, the design criteria for fabricated tissues which mimic normal and tumor vessel network geometry (see FIG. 1) include, but are not limited to, a plurality of branched vessels ranging in size from tens to hundreds of micrometers in diameter and substantially smooth inner walls that may minimize frictional drag and turbulence during fluid flow. The fluidic channels created by the methods of the present invention may have a cross-section of any shape, including but not limited to, circular, oval, or rectangular cross-section, or a combination thereof. In some embodiments, the fluidic channels have a channel volumetric density of between 5% and 95%. By way of example and not of limitation, the network will likely have all interstitial volume within a distance of at most 500 µm of nearby network element. Further by example, the final composition will have living cells within 500 µm of a nearby fluidic channel where cellular nutrients and cellular waste are transported into and out of the network.

The present disclosure provides numerous ways to fabricate substantially interconnected vascular networks with, among other things, the control needed for tissue engineering applications. Additionally, the equipment used for these techniques may be substantially less expensive than lithography equipment and may present numerous technical advantages. Among the many advantages of the methods of the present disclosure is that they may be much faster than photolithography for creating substantially interconnected vascular networks. Additionally, they may produce vascular networks with substantially smooth inner walls, which may adequately mimic native vasculature for tissue and organ engineering applications.

Moreover, the fabrication of vascular networks with substantially cylindrical cross-sections and smooth inter-vessel junctions may readily facilitate seeding endothelial cells in the vascular compartment to form a complete endothelial lining throughout part or all of the vascular network. This endothelial cell layer lining the vascular network may substantially facilitate blood flow by minimizing or eliminating blood clotting.

Thus, the present disclosure provides methods for creating substantially interconnected vascular networks that may mimic the vasculature of normal or diseased tissue for creating in vitro models of tissues or organs. The present disclosure is potentially directly translatable in vivo for medical applications, as well as for numerous research and development efforts currently being investigated in the scientific community, such as mechanistic studies of organ development, angiogenesis, vascular remodeling, stem cell and vascular niches, and diseased states of each of these categories, such as for in vitro models of cancer malignancy. For tissue engineering and whole organ replacement, the speed, efficiency, and highly parallel nature of the methods of the present disclosure may make it foreseeable to create large, physiologically relevant model vasculature (e.g., 750 mL of vasculature that is reminiscent of an adult human liver) in the span of a few hours of fabrication time. Combined with the inexpensive nature of the equipment required, the methods of the present disclosure may lend itself well to, among other things, mass production of whole organ vasculature.

To facilitate a better understanding of the present invention, the following examples of specific embodiments are given. In no way should the following examples be read to limit or define the entire scope of the invention.

EXAMPLE 1

In one embodiment, in a method wherein electrospinning is used to form a fiber network, a commercially available photoresist (SU-8, Microchem, Newton, Mass.) is used as a model material for the fiber network formation and subsequent stripping to reveal substantially interconnected vessel networks. SU-8 photoresist is easily stripped in a variety of organic solvents (including, but not limited to, N-methylpyrrolidinone, ethanol, and acetone), if the resist has not been developed or hard baked. A range of viscosities of photoresist are easily attained simply by mixing two commercially available preparations (e.g. SU-8 2002 and SU-8 2050) in pre-determined ratios (e.g. by weight).

SU-8 2002 (5.05 grams) and SU-8 2050 (10.15 grams) were added to a 40 mL UV-opaque glass vial. The photoresist mixture was stirred with a magnetic stir bar for 10 minutes until a uniform viscosity was attained and allowed to stand at room temperature until all bubbles had left the liquid phase. 5 mL of this mixture was then loaded into a 12 mL plastic syringe which was fitted with an 18-gauge blunt end steel syringe needle. This loaded syringe was mounted onto a syringe pump for electrospinning.

Electrospinning of photoresist follows the general electrospinning method described previously for polycaprolactone (Pham et al., 2006), optionally without the extra copper wire ring. The stability of the Taylor cone is principally controlled by properties of the liquid such as its viscosity or conductivity. The following parameters result in the desired unstable Taylor cone. Briefly, a syringe pump (Cole Parmer, Vernon Hills, Ill.), high voltage power supply (Gamma High Voltage Research, Ormond Beach, Fla.), and a square (4"), grounded copper plate were setup with a photoresist flow rate of 5 mL/hr, a voltage of 20 kV, and an air distance of 10 cm between the syringe tip and the grounded copper plate. A square (4") glass plate was placed immediately in front of the copper plate to collect electrospun fibers. Importantly, these parameters resulted in an unstable Taylor cone, leading to a range of fiber diameters (380 nm up to 5 µm) as shown in FIG. 2A. Varying these parameters such as by using a more viscous material mixture or a decreased flow rate or distance can be used to create a stable Taylor cone and a vascular network with much more uniform fiber diameters reminiscent of capillary beds. Larger fibers can be generated by increasing the viscosity, shortening the distance for collection, and/or modifying a range of other parameters.

Figure 1A:
FIG. 1A is an image depicting fluorescence imaging of normal brain vasculature.
Figure 1B:
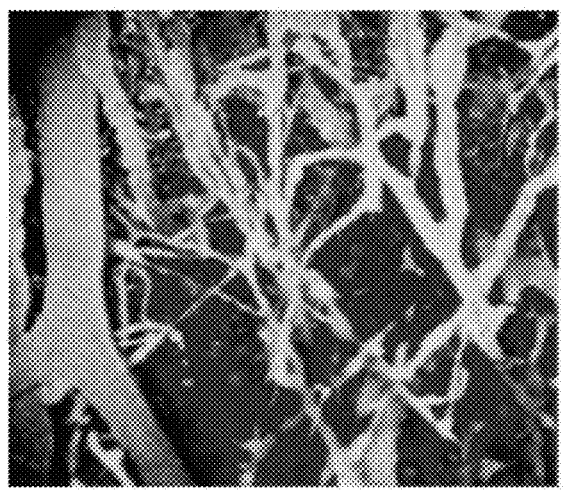
FIG. 1B is an image depicting fluorescence imaging of glioblastoma brain tumor vasculature.
Figure 2B:
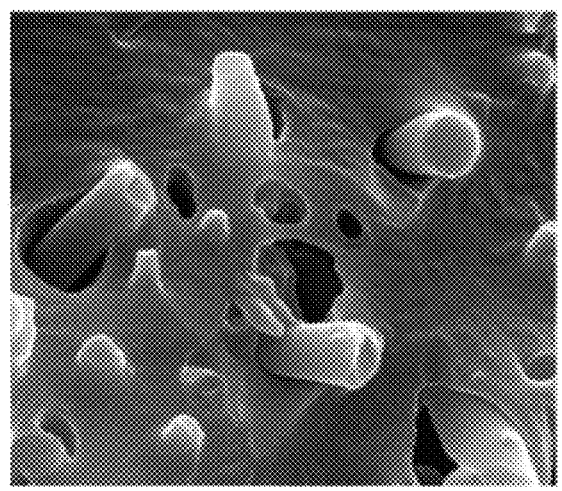
FIG. 2B is an image depicting the void space of the fiber network filled with a biomaterial of interest. Here, fibers are seen in cross-section protruding from the filler material.
Figure 2C:
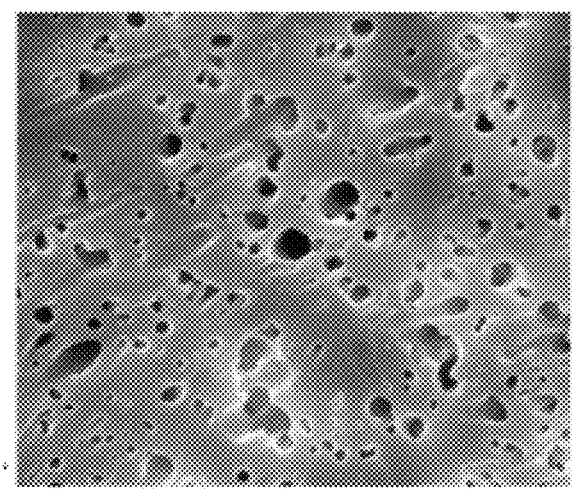
FIG. 2C is an image depicting selective wet etching or dissolution of the fibers, which reveals channels that are precise replica molds of the original fiber network.
Figure 2D:
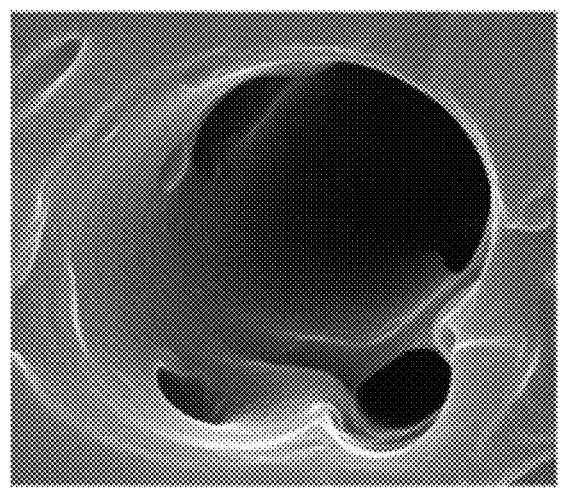
FIG. 2D is a magnification of FIG. 2C, which reveals branched, interconnected channels with smooth inner walls reminiscent of native vasculature.

The resulting fiber network (FIG. 2A) was then backfilled with polydimethylsiloxane (PDMS) before being subjected to wet chemical etching or dissolution. A PDMS prepolymer mixture (Sylgard 184, Dow Corning) was prepared by mixing the as-provided base and initiator in a 10:1 w/w ratio as recommended by the manufacturer. This mixture was degassed at room temperature in a 30 in Hg vacuum. The PDMS prepolymer mixture was then brought to atmospheric pressure and poured over a sample of the fiber network described above that was placed in a plastic petri dish. Evacuation to a ≥30 in Hg vacuum at room temperature allowed the liquid PDMS prepolymer to infiltrate the fiber mat completely until no more air bubbles emerged from the fiber mat. The mixed material phases were then brought to atmospheric pressure and incubated at room temperature for 4 days to allow the PDMS to fully cure and harden without crosslinking the photoresist. PDMS was chosen as a model filler material because it does not shrink under the high vacuum of an electron microscope. Therefore, the images in FIG. 2 provide an accurate assessment of the backfilling process with few artifacts. A cross-section slice through the fibers reveals complete filling of the void volume around the photoresist fibers with PDMS (FIG. 2B). A portion of these embedded fibers were wet etched and removed from the PDMS by stirring the embedded fibers in 1 L of acetone for 6 hours (acetone can dissolve the photoresist fibers and can also swell and infiltrate the PDMS polymer). Examination of the PDMS revealed successful wet etching and dissolution of the photoresist fibers, leaving a dense, interconnected vessel network in the PDMS material (FIGS. 2C and 2D) that is reminiscent of normal and diseased vasculature (FIG. 1).

EXAMPLE 2

In one embodiment, a sugar solution is created (5 g sucrose, 620 mg glucose, 5.2 mL water) and heated to the hard-crack stage (~154° C.), then poured into ~1 cm diameter cylindrical molds (~10 mL volume), and cooled to room temperature as a translucent sugar-glass cylinder. The solid sugar cylinder is then placed into a commercially available hot glue gun, then warmed to partially liquefy for controlled extrusion by hand or with a commercially available 3D printer (MakerBot Industries, Cupcake CNC).

Figure 3:
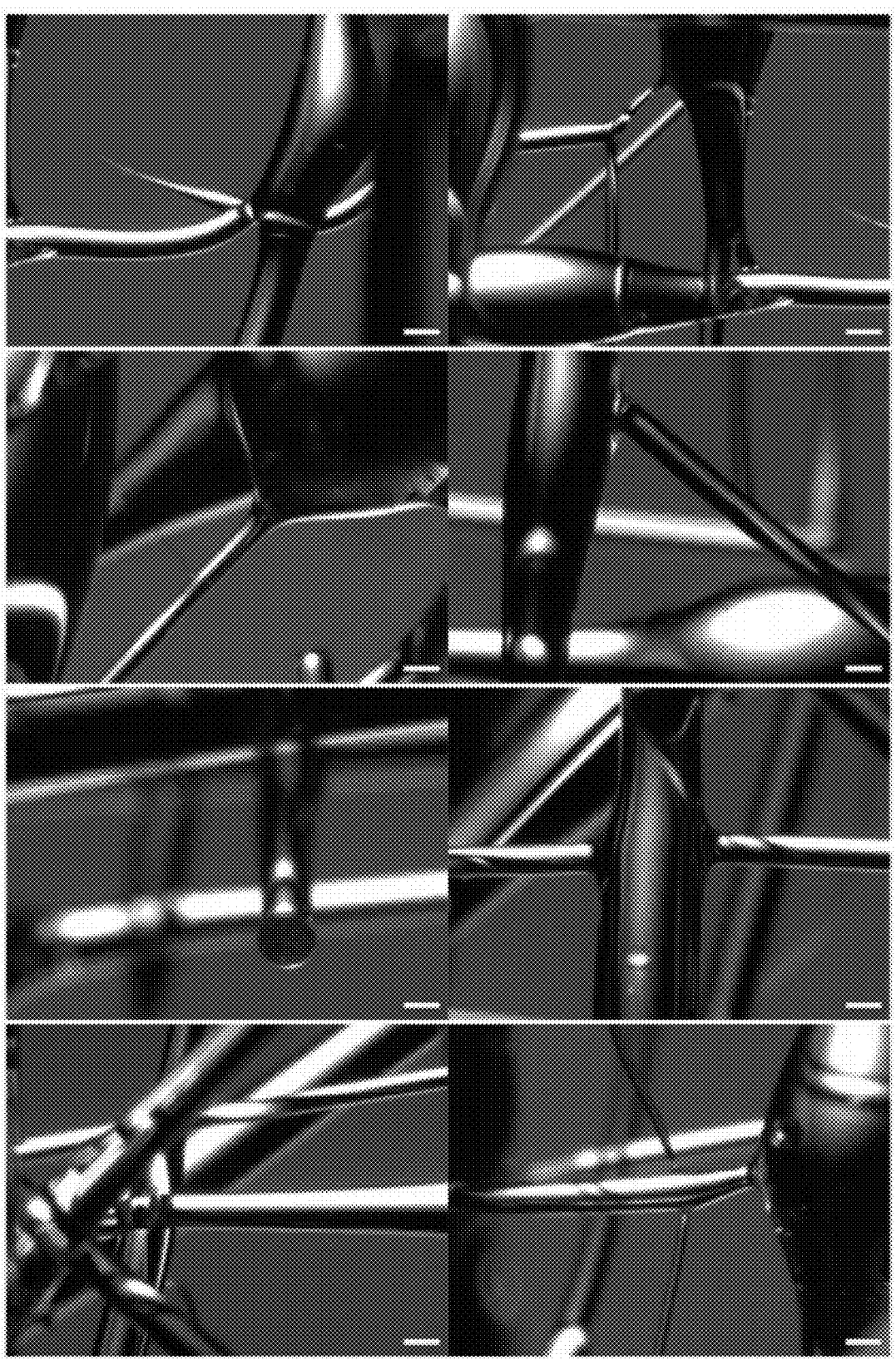
FIG. 3 is several images depicting 3D interconnected sugar filaments created by controlled melt extrusion. Scale bar=200 μm.
Figure 4A:
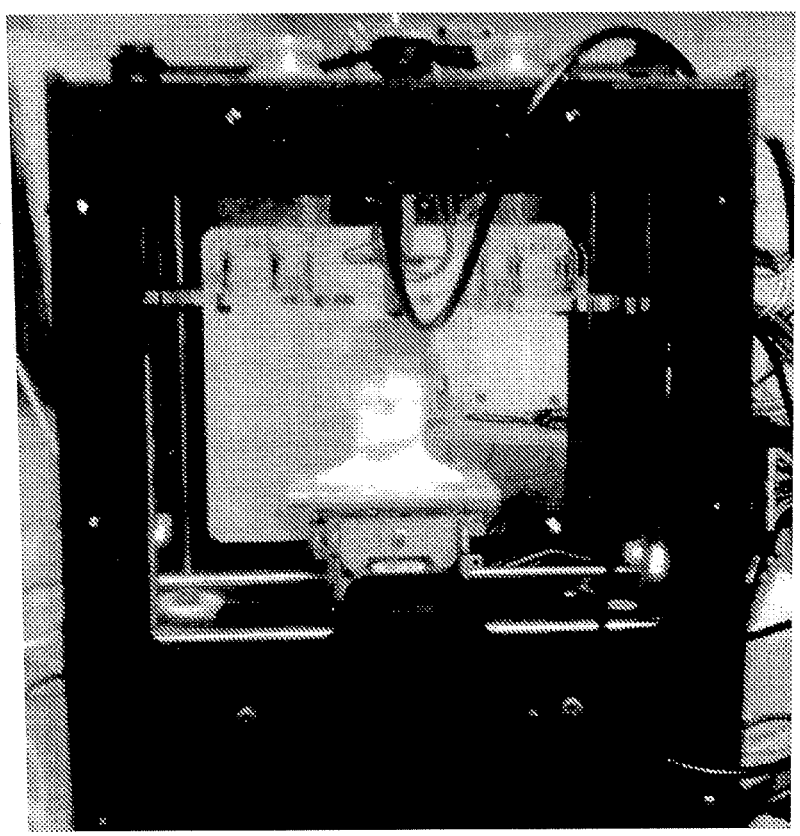
FIG. 4A is an image depicting a MakerBot Industries CupCake CNC, which was used to robotically control 3D deposition of filamentous networks
Figure 4B:
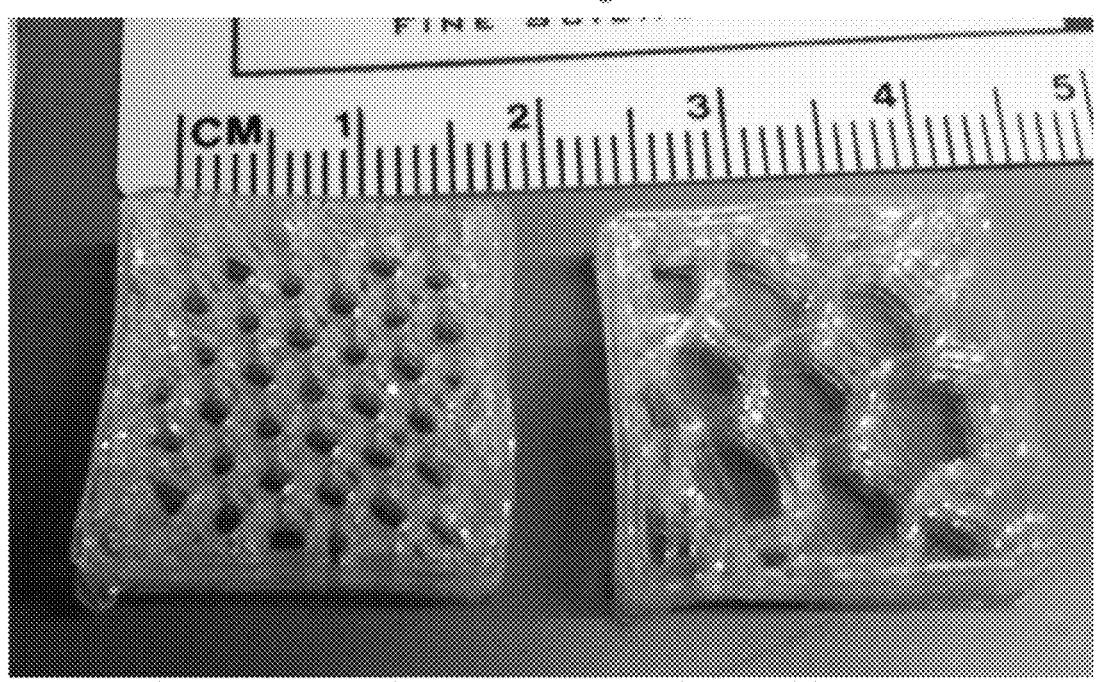
FIG. 4B is an image depicting sample vascular networks.

FIG. 3 shows the microstructure of interconnected sugar filaments. FIG. 4A shows the layout of the commercially available 3D printer. Filaments can be generated which span at least the complete range of diameters found in in vivo human vasculature, from centimeters in diameter down to tens of microns or smaller. (See FIG. 4B). The filamentous network is then optionally surface coated to aid in stabilization during embedding at the next step. The surface coating can optionally be a part of the final 3D construct (mimic of basement membrane found lining all blood vessels in humans) or be selectively etched using a variety of standard solvent-based techniques. In this example, a 3D filamentous network is briefly dipped in a 0.1 g/mL solution of polylactic acid (PLA) in dichloromethane to provide a thin and uniform coating across surface of the network.

Figure 5A:
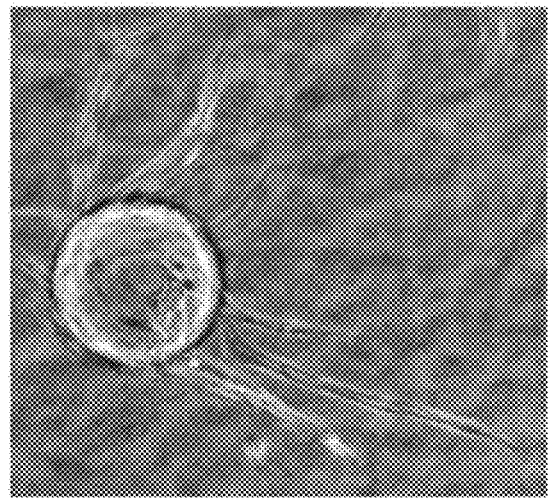
FIG. 5A is an image depicting human endothelial cells inside a fibrin-based gel.
Figure 5B:
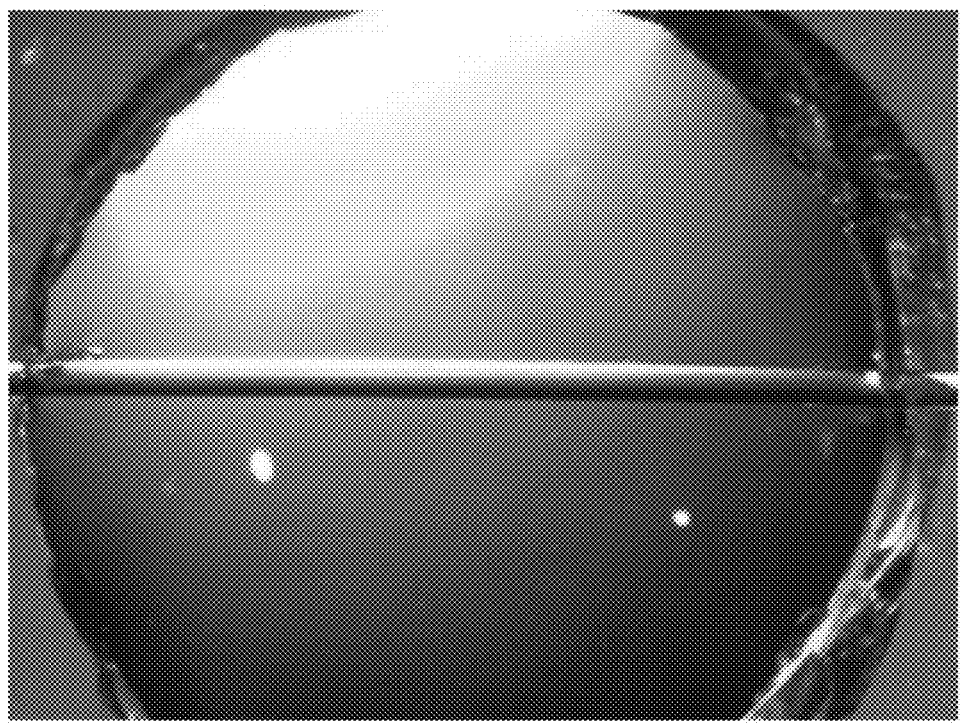
FIG. 5B is an image depicting PLA-coated sugar filament inside a fibrin-based gel.

The surface-coated or uncoated interconnected fiber network is then backfilled with the final construct material of interest. In one example, the sugar-based filament network is submerged in an aqueous solution of extracellular matrix proteins (2.5-20 mg/mL Fibrin), optionally containing living cells which survive the gelation/solidification process. In another example, the filament network is submerged in an aqueous solution at 4° C. containing poly(ethylene glycol) diacrylate (PEGDA, MW 3400, 10 wt %) with photoinitiator (0.5% Irgacure 2959, 5 µl/mL) while being exposed to UV light (320-510 nm light, 100 mW/cm2 measured at 365 nm) to crosslink a PEG-based hydrogel. Importantly, these conditions allow both living human cells and the filamentous network to survive the encapsulation process (FIGS. 5A and 5B).

Figure 6A:
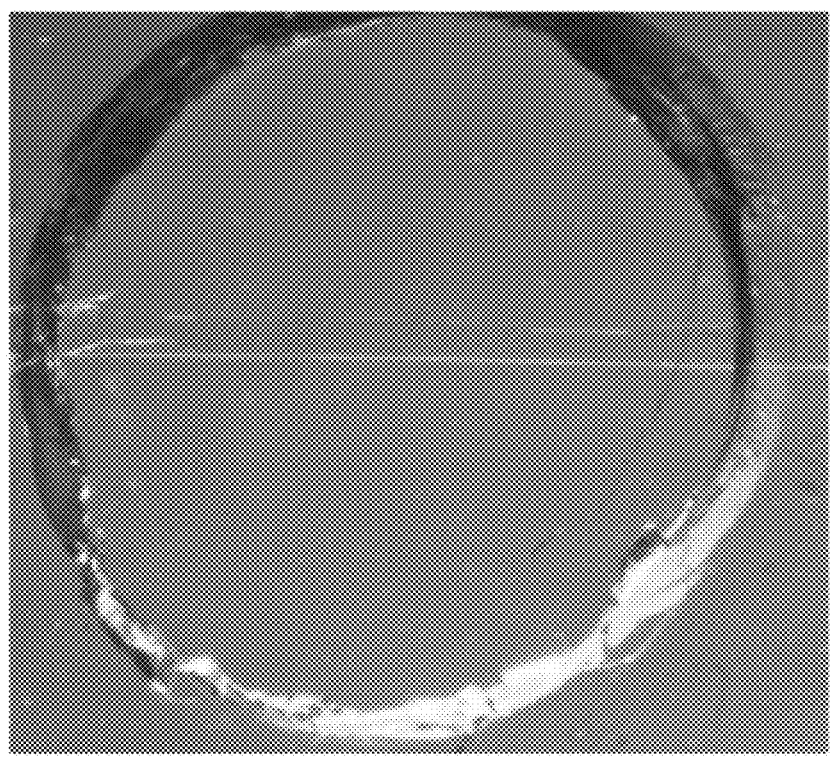
FIG. 6A is an image depicting sugar filament embedded in a fibrin gel which was etched in dilute and biocompatible saline solution to reveal transparent fluidic networks within the biocompatible material of interest. Scale Bar=500 μm.
Figure 6B:
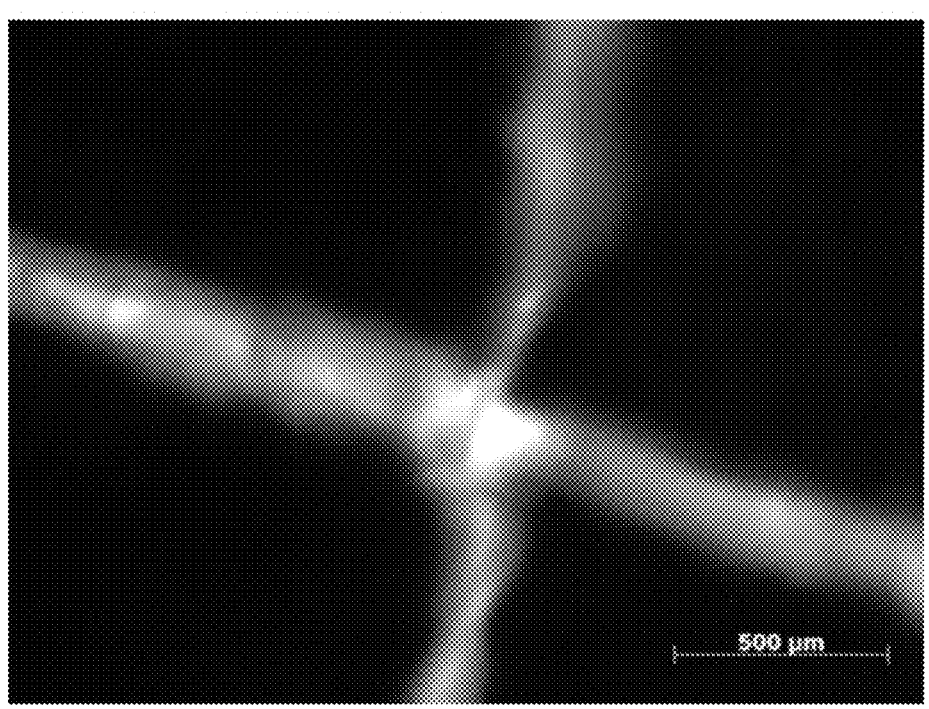
FIG. 6B is an image depicting very small microfluidic networks which were also etched in dilute and biocompatible saline solution to allow flow of fluorescent rhodamine-labeled dextran solutions in saline through the crossing filament junctions shown. Scale Bar=500 μm.
Figures 7A, 7B, 7C, 7D, 7E, 7F:
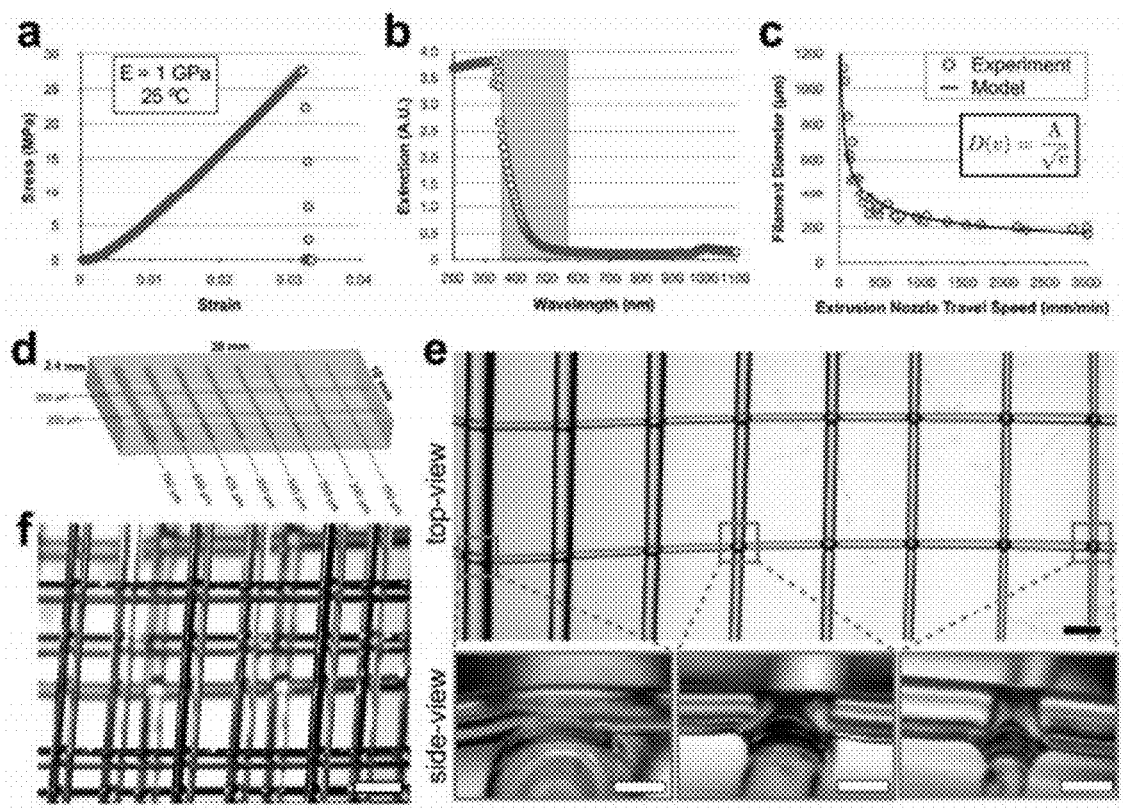
FIG. 7A is a graph depicting the Stress-strain curve from uniaxial compression testing of a carbohydrate glass material, and indicates the carbohydrate glass is a stiff and brittle material at 25° C., with Young's modulus=1 GPa (measured in the linear regime), maximum strength of 28 MPa, maximum strain of 3.25%.
FIG. 7B is a graph depicting the optical extinction for a 1 cm sample of carbohydrate glass and indicates that the material transmits light wavelengths commonly used during biocompatible imaging and photopolymerization (365-550 nm, shaded box).
FIG. 7C is a graph demonstrating that during thermal extrusion and 3D printing, filament diameter can be controlled by the travel speed of the extrusion nozzle and follows a simple power law from glass fiber drawing (equation inset).
FIG. 7D is a drawing depicting the architectural design of a multiscale carbohydrate glass lattice (green).
FIG. 7E is an image depicting a top view of the multiscale architectural design in FIG. 7D that was 3D printed in carbohydrate glass (scale bar=1 mm). Interfilament melt fusions are magnified and shown in side-view (scale bars=200 μm).
FIG. 7F is an image showing that multilayered lattices are fabricated in minutes with precise lateral and axial positioning resolution (scale bar=1 mm).

Etching of the filamentous network while maintaining human cell viability was done by exposing the sugar-based fiber network to normal cell media or dilute biocompatible saline solutions (1× Phosphate Buffered Saline). The sugar-based network completely dissolves, leaving behind an interconnected vascular network which can be perfused with growth media, pharmaceutical agents, oxygenated human blood, or other liquids (FIGS. 6A and 6B).

EXAMPLE 3

A mixture of 100 g isomalt, 10 g dextran (86 kDa), and 50 mL reverse osmosis water (≥18 megaohm; Millipore) was warmed to 165-185° C. with rapid stirring to remove most of the water and form a liquid glass. The hot mixture was poured into a 50 mL glass syringe that was maintained at 110° C. The syringe was mounted on a custom modified RepRap Mendel 3D printer with associated electronics (Generation3, MakerBot). Custom Python scripts were developed to generate the 3D motion control GCode used to drive the machine via ReplicatorG open source software. Fiber networks, which in this example are carbohydrate glass lattices, were 3D printed at 110° C. under nitrogen pressure with pneumatic control through a 16-gauge (1.2 mm ID) steel nozzle, cooled to 45° C. and immersed in a 200 mg/mL solution of poly(D-lactide-co-glycolide) (PDLGA; Purac, Amsterdam) in chloroform for 1 min. FIGS. 7A-7F contain graphs and images depicting carbohydrate glass material properties and lattice architecture formation.

Carbohydrate glass lattices can be encapsulated (backfilled) with a biomaterial comprising living cells on the same day the lattices are fabricated. To encapsulate lattices and form living cell-laden gels with patterned vascular architecture, a gel prepolymer solution with a suspension of living cells and/or cellular aggregates is poured to encapsulate the carbohydrate glass lattice. FIGS. 8A-8D contain images depicting how monolithic tissue constructs containing patterned vascular architectures and living cells can be fabricated and characterized.

Resulting cell-laden gels with open vascular architectures can optionally be seeded with living endothelial cells such as human umbilical vein endothelial cells (HUVECs) by injecting a saline solution containing HUVECs in suspension into the vascular architecture. After 1 hour in culture to allow HUVECs to adhere to part of the vascular network, the gels are rotated 180° about the x- or y-axis to allow HUVECs to adhere to the remaining surface of the vascular network. This process may be repeated as needed to ensure complete coating.

Tissue culture of cellularized gels that contain endothelial cells in their vascular compartment can be cultured in vitro to allow sufficient time for the endothelial cells to form a complete endothelium lining the prescribed regions of the vascular architecture that are desired to have an endothelium.

Resulting engineered tissues which substantially resemble native mammalian tissues and organs may be implanted in vivo for further study or optimization of engineered tissue integration with host tissue and/or anastomosis of engineered vascular architecture with native host vasculature. FIGS. 9A-9C contains images depicting how perfusion channels can sustain cellular metabolic function in the core of thick, densely populated tissue constructs.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

REFERENCES

1. Atala A, Bauer S B, Soker S, Yoo J J, Retik A B. "Tissue-engineered autologous bladders for patients needing cystoplasty." Lancet. 2006 Apr. 15; 367(9518): 1241-6. PMID: 16631879.
2. Bikram M, Fouletier-Dilling C, Hipp J A, Gannon F, Davis A R, Olmsted-Davis E A, West J L. "Endochondral Bone Formation from Hydrogel Carriers Loaded with BMP2-transduced Cells." Ann Biomed Eng. 2007 May; 35(5):796-807. PMID: 17340196.
3. Czaplewski D A, Kameoka J, Mathers R, Coates G W, Craighead H G. "Nanofluidic channels with elliptical cross sections formed using a nonlithographic process." Appl Phys Lett. 2003 Dec. 8; 83(23):4836-8.
4. Dagalakis N, Flink J, Stasikelis P, Burke J F, Yannas I V. "Design of an artificial skin Part III. Control of pore structure." J Biomed Mater Res. 1980 July; 14(4):511-28. PMID: 7400201
5. Golden A P, Tien J. "Fabrication of microfluidic hydrogels using molded gelatin as a sacrificial element." Lab Chip. 2007 June; 7(6):720-5. PMID: 17538713.
6. Gratson G M, Xu M, Lewis J A. "Microperiodic structures: direct writing of three-dimensional webs." Nature. 2004 Mar. 25; 428(6981):386. PMID: 15042080.
7. Gray D S, Tien J, Chen C S. "High-conductivity elastomeric electronics." Adv Mater. 2004 May; 16(5):393-7.
8. Hahn M S, Miller J S, West J L. "Three-dimensional biochemical and biomechanical patterning of hydrogels for guiding cell behavior." Adv Mat. 2006 October; 18(20):2679-84.
9. Heimbach D, Luterman A, Burke J, Cram A, Herndon D, Hunt J, Jordan M, McManus W, Solem L, Warden G et al. "Artificial dermis for major burns. A multi-center randomized clinical trial." Ann Surg. 1988 September; 208 (3):313-20. PMID: 3048216.
10. Johnson P C, Mikos A G, Fisher J P, Jansen J A. "Strategic directions in tissue engineering." Tissue Eng. 2007 December; 13(12):2827-37. PMID: 18052823.
11. Jun H W, West J L. "Endothelialization of Microporous YIGSR/PEG-Modified Polyurethaneurea." Tissue Eng. 2005 July-August; 11(7-8):1133-40. PMID: 16144449
12. Khademhosseini A, Langer R. "Microengineered hydrogels for tissue engineering." Biomaterials. 2007 December; 28(34):5087-92. PMID: 17707502.
13. Ko H C, Milthorpe B K, McFarland C D. "Engineering thick tissues—the vascularisation problem." Eur Cell Mater. 2007; 14:1-18; discussion 18-9. PMID: 17654452.
14. Koike N, Fukumura D, Gralla O, Au P, Schechner J S, Jain R K. "Tissue engineering: creation of long-lasting blood vessels." Nature. 2004 Mar. 11; 428(6979):138-9. PMID: 15014486.
15. Li D, Herricks T, Xia Y. "Magnetic nanofibers of nickel ferrite prepared by electrospinning" Appl Phys Lett. 2003 Dec. 1; 83(22):4586-8.
16. Li D, Wang Y, Xia Y. "Electrospinning nanofibers as uniaxially aligned arrays and layer-by-layer stacked films." Adv Mater. 2004 February; 16(4):361-6.
17. Ling Y, Rubin J, Deng Y, Huang C, Demirci U, Karp J M, Khademhosseini A. "A cell-laden microfluidic hydrogel." Lab Chip. 2007 June; 7(6):756-62. PMID: 17538718.
18. Liu Tsang V, Chen A A, Cho L M, Jadin K D, Sah R L, DeLong S, West J L, Bhatia S N. "Fabrication of 3D 19. Nishida K, Yamato M, Hayashida Y, Watanabe K, Yamamoto K, Adachi E, Nagai S, Kikuchi A, Maeda N, Watanabe H, Okano T, Tano Y. "Corneal reconstruction with tissue-engineered cell sheets composed of autologous oral mucosal epithelium." N Engl J. Med. 2004 Sep. 16; 351(12):1187-96. PMID: 15371576.
20. Pham Q P, Sharma U, Mikos A G. "Electrospun poly (epsilon-caprolactone) microfiber and multilayer nanofiber/microfiber scaffolds: characterization of scaffolds and measurement of cellular infiltration." Biomacromolecules. 2006 October; 7(10):2796-805. PMID: 17025355.
21. Siegel A C, Bruzewicz D A, Weibel D B, Whitesides G M. "Microsolidics: Fabrication of three-dimensional metallic microstructures in poly(dimethylsiloxane)." Adv Mater. 2007 March; 19(5):727-33.
22. Therriault D, Shepherd R F, White S R, Lewis J A. "Fugitive Inks for Direct-Write Assembly of 3-D Microvascular Networks." Advanced Materials. 2005; 17(4): 395-99.
23. Yannas I V, Burke J F, Orgill D P, Skrabut E M. "Wound tissue can utilize a polymeric template to synthesize a functional extension of skin" Science. 1982 Jan. 8; 215 (4529):174-6. PMID: 7031899.

What is claimed is:

1. A method of forming a substantially interconnected vascular network, comprising:
    forming a fiber network comprising a plurality of fibers and a void space, wherein the plurality of fibers is capable of dissolving or degrading in water;
    surface coating the plurality of fibers with a surface coating material, wherein the surface coating material does not backfill the void space;
    backfilling the void space of the fiber network with an aqueous solution comprising a biomaterial, wherein the biomaterial and the surface coating material are different materials;
    cross-linking the biomaterial to form a hydrogel in the void space; and
    removing the fibers to form a substantially interconnected vascular network comprising fluidic channels wherein the fibers comprise at least one material selected from the group consisting of: photoresist, agarose, gelatin, carbohydrates, sucrose, glucose, fructose, lactose, isomalt, dextran, cellulose, methylcellulose, poly(lactic acid), poly(ethylene glycol), and chitosan, and
    wherein the surface coating material comprises at least one material selected from the group consisting of: polylactic acid, a solution of polylactic acid in dichloromethane, poly(lactic co-glycolic acid), a solution of poly(lactic co-glycolic acid) in chloroform, collagen, gelatin, zein, shellac, a starch, and petroleum jelly.

2. The method of claim 1 wherein forming a fiber network comprises using electrospinning with a Taylor cone that produces fiber diameters with a standard deviation greater than about plus or minus 10%, a plurality of melt extrusion dies or melt extrusion speeds, a three-dimensional printer, or a combination thereof.

3. The method of claim 1 wherein the biomaterial comprises at least one biomaterial selected from the group consisting of: a polyamide, poly(2-hydroxy ethyl methacrylate), poly(vinyl alcohol), polyacrylamide, poly(ethylene glycol), a polyurethane, collagen, agarose, albumin, alginate, chitosan, starch, hyaluronic acid, gelatin, fibrin, matrigel, glycerol, glycol, mannitol, inositol, xylitol, adonitol, glycine, arginine, biological polymeric molecules, albumin, peptide amphiphiles, and monomers, dimers, and oligomers thereof.

4. The method of claim 1 wherein the aqueous solution further comprises at least one component selected from the group consisting of: a suspension of living cells, a protein, DNA, a nanoparticles, and a moiety used for drug delivery.

5. The method of claim 1 wherein the aqueous solution further comprises a human bone morphogenic protein or a DNA plasmid that encodes for a protein that stimulates mineralization and bone formation.

6. The method of claim 1 wherein the step of removing the fibers is performed by wet etching or dissolution.

7. The method of claim 1 wherein the step of removing the fibers is performed by degradation.

8. The method of claim 1 wherein forming a fiber network comprises using electrospinning with a Taylor cone that produces fiber diameters with a standard deviation greater than about plus or minus 10%.

9. The method of claim 1 wherein forming a fiber network comprises using a plurality of melt extrusion dies or varying melt extrusion speeds.

10. The method of claim 1 wherein forming a fiber network comprises using a three-dimensional printer.

11. The method of claim 1 wherein the fiber network is a non-woven fiber network.

12. The method of claim 1 wherein the aqueous solution further comprises a suspension of living cells; and wherein the step of removing the fibers does not damage the living cells.

13. The method of claim 1 wherein the plurality of fibers are hollow.

14. The method of claim 1 wherein the plurality of fibers are solid.

15. The method of claim 1 further comprising applying heat to at least a portion of the fiber network prior to backfilling the void space of the fiber network.

* * * * *